(12) United States Patent
Soutsuka et al.

(10) Patent No.: US 12,257,095 B2
(45) Date of Patent: Mar. 25, 2025

(54) X-RAY DIAGNOSTIC APPARATUS AND CONTROL METHOD THEREOF

(71) Applicant: CANON MEDICAL SYSTEMS CORPORATION, Otawara (JP)

(72) Inventors: Norio Soutsuka, Nasushiobara (JP); Takahiro Inagaki, Nasushiobara (JP); Motohiro Sato, Nasushiobara (JP); Tomio Maehama, Nasushiobara (JP); Hiroshi Nakayama, Utsunomiya (JP); Takumi Kudo, Nasushiobara (JP); Yusuke Okumura, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 412 days.

(21) Appl. No.: 17/456,023

(22) Filed: Nov. 22, 2021

(65) Prior Publication Data

US 2022/0160320 A1   May 26, 2022

(30) Foreign Application Priority Data

Nov. 24, 2020   (JP) .................................. 2020-194175

(51) Int. Cl.
   *A61B 6/06*   (2006.01)
   *A61B 6/00*   (2006.01)
   *A61B 6/04*   (2006.01)

(52) U.S. Cl.
   CPC .............. *A61B 6/54* (2013.01); *A61B 6/0407* (2013.01); *A61B 6/06* (2013.01); *A61B 6/487* (2013.01)

(58) Field of Classification Search
   CPC ........... A61B 6/54; A61B 6/0407; A61B 6/06; A61B 6/487; A61B 6/481
   See application file for complete search history.

(56) References Cited

U.S. PATENT DOCUMENTS

2003/0169847 A1*   9/2003   Karellas ................. A61B 6/482
                                                                   378/98.3
2012/0269318 A1*   10/2012   Flohr ..................... A61B 6/032
                                                                   378/16

(Continued)

FOREIGN PATENT DOCUMENTS

JP   2007-159913 A   6/2007
JP   2011-55970 A   3/2011

(Continued)

OTHER PUBLICATIONS

Translation of JP2011055970A (Year: 2011).*
Japanese Office Action issued May 7, 2024 in Japanese Application No. 2020-194175, therein, 4 pgs.

*Primary Examiner* — Dani Fox
*Assistant Examiner* — Mamadou Faye
(74) *Attorney, Agent, or Firm* — Oblon, McClelland, Maier & Neustadt, L.L.P.

(57) ABSTRACT

According to one embodiment, an X-ray diagnostic apparatus includes an X-ray tube, an X-ray variable diaphragm, an X-ray detector, and processing circuitry. The X-ray tube irradiates X-rays. The X-ray variable diaphragm limits an irradiation region of the X-rays. The X-ray detector detects the X-rays that have passed through an object. The processing circuitry controls a movement of the X-ray tube, the X-ray detector, and an aperture of the X-ray variable diaphragm such that, when the irradiation region on the X-ray detector moves within an imaging range, a movement velocity of the irradiation region relative to the imaging range is maintained constant.

9 Claims, 11 Drawing Sheets

(56) References Cited

U.S. PATENT DOCUMENTS

2015/0250441 A1* 9/2015 Okuno .................. A61B 6/547
378/62
2017/0119338 A1* 5/2017 Merckx ................. A61B 6/469

FOREIGN PATENT DOCUMENTS

JP       2011055970 A * 3/2011 .............. A61B 6/00
JP       2016-214362 A   12/2016

* cited by examiner

X-RAY DIAGNOSTIC APPARATUS AND CONTROL METHOD THEREOF

CROSS-REFERENCE TO RELATED APPLICATIONS

This application claims the benefit of priority of Japanese Patent Application No. 2020-194175, filed Nov. 24, 2020, the entire contents of which are incorporated herein by reference.

FIELD

Embodiments described herein relate generally to an X-ray diagnostic apparatus and a control method thereof.

BACKGROUND

In X-ray diagnostic apparatus, the area to be observed may cover a wide range, such as the gastrointestinal tract or lower limb blood vessels. For example, the X-ray diagnostic apparatus tracks the movement of the contrast medium as it moves within the imaging range from upstream to downstream. In this case, with the X-ray detector stopped, the user can observe the entire area to be observed by controlling the X-ray variable diaphragm to move the X-ray irradiation region for X-ray fluoroscopy.

However, the desired imaging range of the user may not fit into the size of the X-ray detector. In this case, in order to prevent the irradiation region from extending outside the X-ray detector, when the moving irradiation region reaches the downstream end of the X-ray detector, the user must suspend observation, move the X-ray detector to the downstream side, manipulate the X-ray variable diaphragm such that the irradiation region is positioned at the upstream end of the moved X-ray detector, and then resume observation of the region to be observed. In this case, the user is forced to suspend the observation and perform complicated positioning of the imaging system. Further, the user may lose sight of the observation target during the position adjustment. Furthermore, since the examination time becomes longer due to the position adjustment, the burden on the object increases. In addition, since the X-ray fluoroscopy is continued during the positioning process to support the user, the radiation dose of the object increases.

DETAILED DESCRIPTION

Hereinbelow, a description will be given of an X-ray diagnostic apparatus and a control method thereof according to embodiments of the present invention with reference to the drawings.

In general, according to one embodiment, an X-ray diagnostic apparatus includes an X-ray tube, an X-ray variable diaphragm, an X-ray detector, and processing circuitry. The X-ray tube irradiates X-rays. The X-ray variable diaphragm, limits an irradiation region of the X-rays. The X-ray detector detects the X-rays that have passed through an object. The processing circuitry controls a movement of the X-ray tube, the X-ray detector, and an aperture of the X-ray variable diaphragm such that, when the irradiation region on the X-ray detector moves within an imaging range, a movement velocity of the irradiation region relative to the imaging range is maintained constant.

Figure 1:
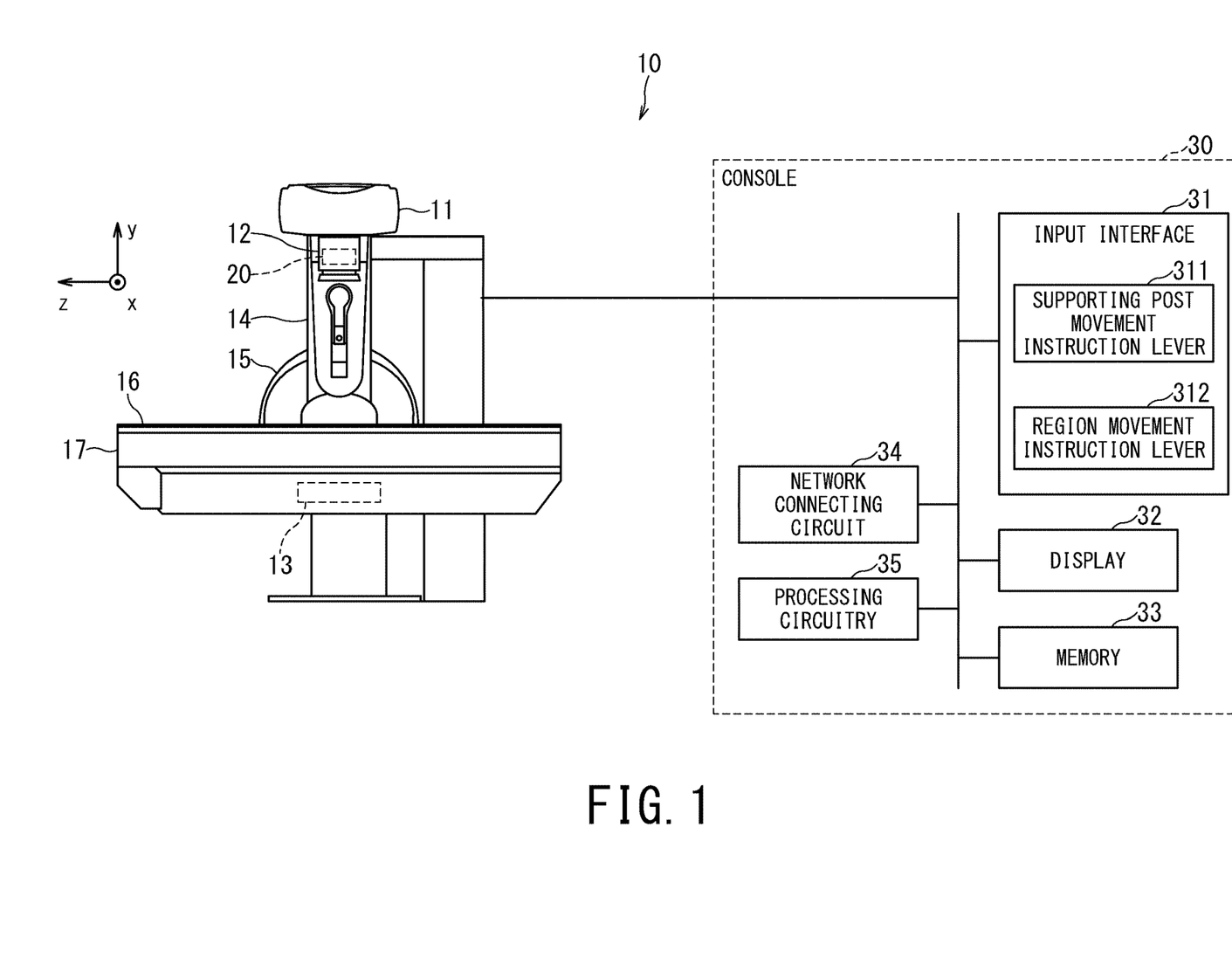
FIG. 1 is a block diagram showing an example of an X-ray diagnostic apparatus according to an embodiment.

FIG. 1 is a block diagram showing an example of an X-ray diagnostic apparatus 10 according to an embodiment. The X-ray diagnostic apparatus 10 according to embodiments can be anything that can perform fluoroscopy and imaging, and includes, for example, X-ray TV apparatuses and X-ray angiography apparatuses. In this embodiment, an example of a case where an X-ray TV apparatus is used as the X-ray diagnostic apparatus 10 is described.

The X-ray diagnostic apparatus 10, as shown in FIG. 1, includes an X-ray source 11, a housing 12 that houses an X-ray variable diaphragm 20 and an X-ray detector 13, a supporting post 14, a supporting post driving mechanism 15, a tabletop 16, a bed 17, and a console 30. In this embodiment, the lateral direction of the tabletop 16 is defined as the x-axis, the normal direction of the tabletop 16 as the y-axis, and the longitudinal direction of the tabletop 16 as the z-axis (see FIG. 1).

The X-ray source 11 is, for example, an X-ray tube to which a voltage is applied by a high-voltage generator (not shown) to generate X-rays. The X-ray tube includes a vacuum tube that irradiates hot electrons from a cathode (filament) to an anode (target) by being applied a high voltage from the high-voltage generator.

The housing 12 is a housing made of metal, houses at least the X-ray variable diaphragm 20, and may also house a region of interest filter (ROI filter). The X-ray source 11 and the housing 12 are supported at one end of the supporting post 14 as shown in FIG. 1.

Figure 2:
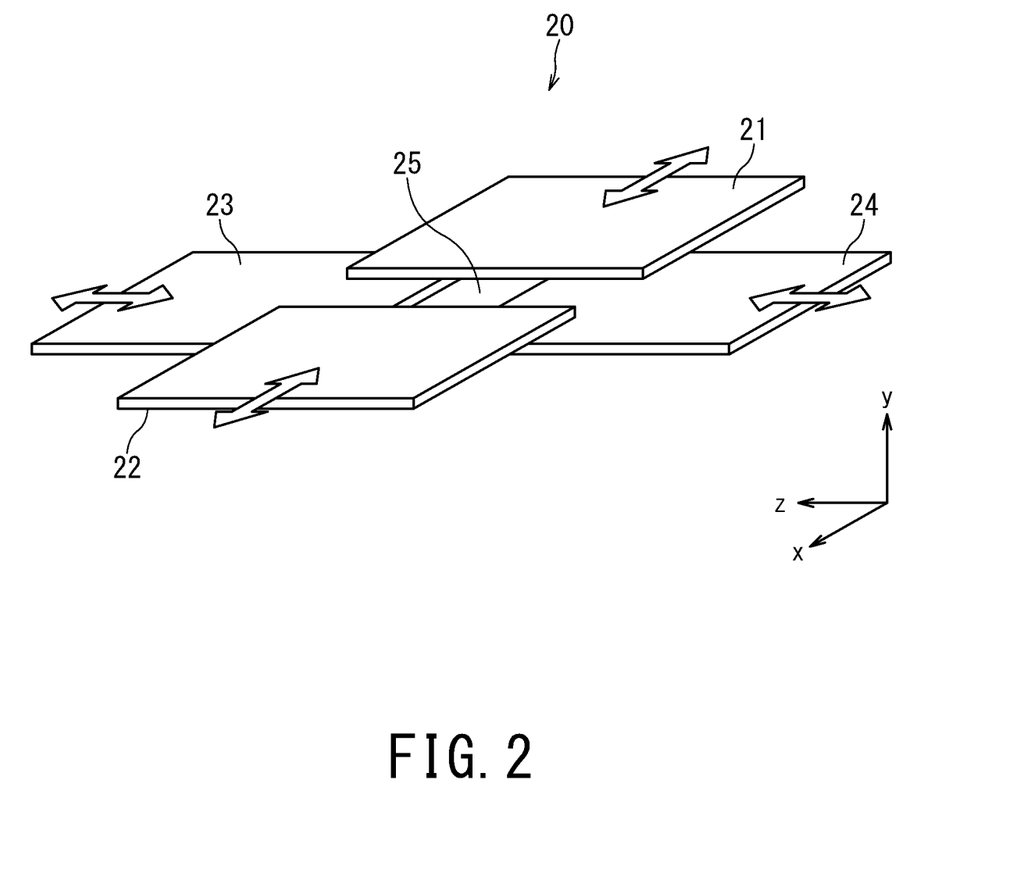
FIG. 2 is a diagram showing an example of an X-ray variable diaphragm.

FIG. 2 is a diagram showing an example of the X-ray variable diaphragm 20.

The X-ray variable diaphragm 20 has an aperture 25 for restricting (narrowing) the irradiation region of X-rays. The X-ray variable diaphragm 20 allows X-rays to pass through the aperture 25, while restricting X-rays through regions other than the aperture 25. The variable diaphragm 20 includes diaphragm blades that include a plurality of blade elements, for example.

The diaphragm blades have, for example, four blade elements 21, 22, 23, and 24 as shown in FIG. 2. The blade elements 21-24 are each composed of a flat lead plate or the like to shield X-rays. The area enclosed by the blade elements 21-24 forms the aperture 25 through which the X-rays pass (see FIG. 2).

By independently moving these blade elements 21-24 parallel to the X-ray source 11, the position of the aperture 25 can be moved parallel to the surface of the tabletop 16 and the size of the aperture 25 can be changed while the supporting post 14 remains stationary and the positions of the X-ray source 11 and the X-ray detector 13 are fixed. Therefore, it is possible to change the position and size of the irradiation region corresponding to the aperture 25 while keeping the positions of the X-ray source 11 and the X-ray detector 13 fixed. The number of blade elements of the diaphragm blades is not limited to four as shown in FIG. 2, and for example, a multi-leaf collimator may be used as the diaphragm blades.

The X-ray detector 13 is supported at the other end of the supporting post 14 such that it is placed opposite the X-ray source 11 and the X-ray variable diaphragm 20 across the object placed on the tabletop 16 of the bed 17. The X-ray detector 13 including a flat panel detector (FPD) detects X-rays irradiated to the X-ray detector 13 through the object, outputs image data of X-ray fluoroscopic images and X-ray radiographic images based on the detected X-rays, and provides the image data to the console 30. The X-ray detector 13 may include an image intensifier, TV camera, and the like.

The supporting post 14 is a supporting member that supports the imaging system including the X-ray source 11, the X-ray variable diaphragm 20, and the X-ray detector 13. The configuration of the X-ray variable diaphragm 20 will be described later using FIG. 2.

The supporting post driving mechanism 15 moves the supporting post 14 in a direction parallel to the surface of the tabletop 16 (for example, in the longitudinal or shortitudinal direction of the tabletop 16) to move the X-ray source 11, X-ray variable diaphragm 20, and X-ray detector 13 as a single unit. The supporting post driving mechanism 15 may also raise and lower the bed 17 together with the tabletop 16 around the x-axis with the supporting post driving mechanism 15 as the center. The supporting post driving mechanism 15 has a motor as a drive source to move the imaging system along the direction parallel to the surface of the tabletop 16 and to raise and lower the bed 17, and has electronic components to control the motor.

The tabletop 16 is provided on the top of the bed 17, and the object is placed on the tabletop 16. The bed 17 may also be provided with shoulder rests, footrests, side hand grips, and the like, for supporting the object. The tabletop 16 is moved along the longitudinal and shortitudinal directions of the tabletop 16 with respect to the bed 17 by the tabletop driving mechanism (not shown). The tabletop driving mechanism has a motor as a drive source to move the tabletop 16 and electronic components to control the motor.

The user may observe the object or perform a medical procedure on the object while checking the real-time X-ray fluoroscopic image acquired by X-ray imaging.

The console 30 is composed of, for example, a general personal computer or workstation, and has an input interface 31, a display 32, a memory 33, a network connecting circuit 34, and processing circuitry 35. The console 30 may not be provided independently, and for example, some of the components 31-35 of the console may be provided in the bed 17.

The input interface 31 includes a general input device such as a trackball, a switch button, a mouse, a keyboard, and a numeric keypad, and outputs signals corresponding to user operations to the processing circuitry 35. The user can set the imaging conditions via the input interface 31. The input interface 31 may also include an exposure switch that controls the on/off of exposure.

The input interface 31 may include a supporting post movement instruction lever 311 that directs the supporting post driving mechanism 15 to move the supporting post 14 in the longitudinal and shortitudinal directions of the tabletop 16. The input interface 31 may also include a region movement instruction lever 312 that directs the direction (including orientation) of the movement of the irradiation region 41 with respect to the tabletop 16.

The display 32 is composed of a general display output device such as a liquid crystal display and an OLED (Organic Light Emitting Diode) display, and displays various information such as fluoroscopic images generated by the processing circuitry 35 based on X-ray imaging.

The memory 33 includes a recording medium that can be read by the processor, such as a magnetic or optical recording medium or semiconductor memory. Some or all of the programs and data stored in the recording medium may be configured to be downloaded by communication via an electronic network.

The network connecting circuit 34 may include a network card having a predetermined printed circuit board, and implements various protocols for information communication according to the form of the network. The network connecting circuit 34 connects the X-ray diagnostic apparatus 10 to other devices according to these various protocols. An electrical connection via an electronic network or the like can be applied to this connection. The term "electronic network" refers to all information and communication networks using telecommunications technology, including wireless or wired hospital LAN (Local Area Network), internet networks, telephone communication networks, optical fiber communication networks, cable communication networks, and satellite communication networks.

The processing circuitry 35 includes a processor that executes the processing for automatic fluoroscopy of the imaging range wider than the width of the X-ray detector while moving the X-ray irradiation region at a constant velocity relative to the object by reading and executing the programs stored in the memory 33.

Figure 3:
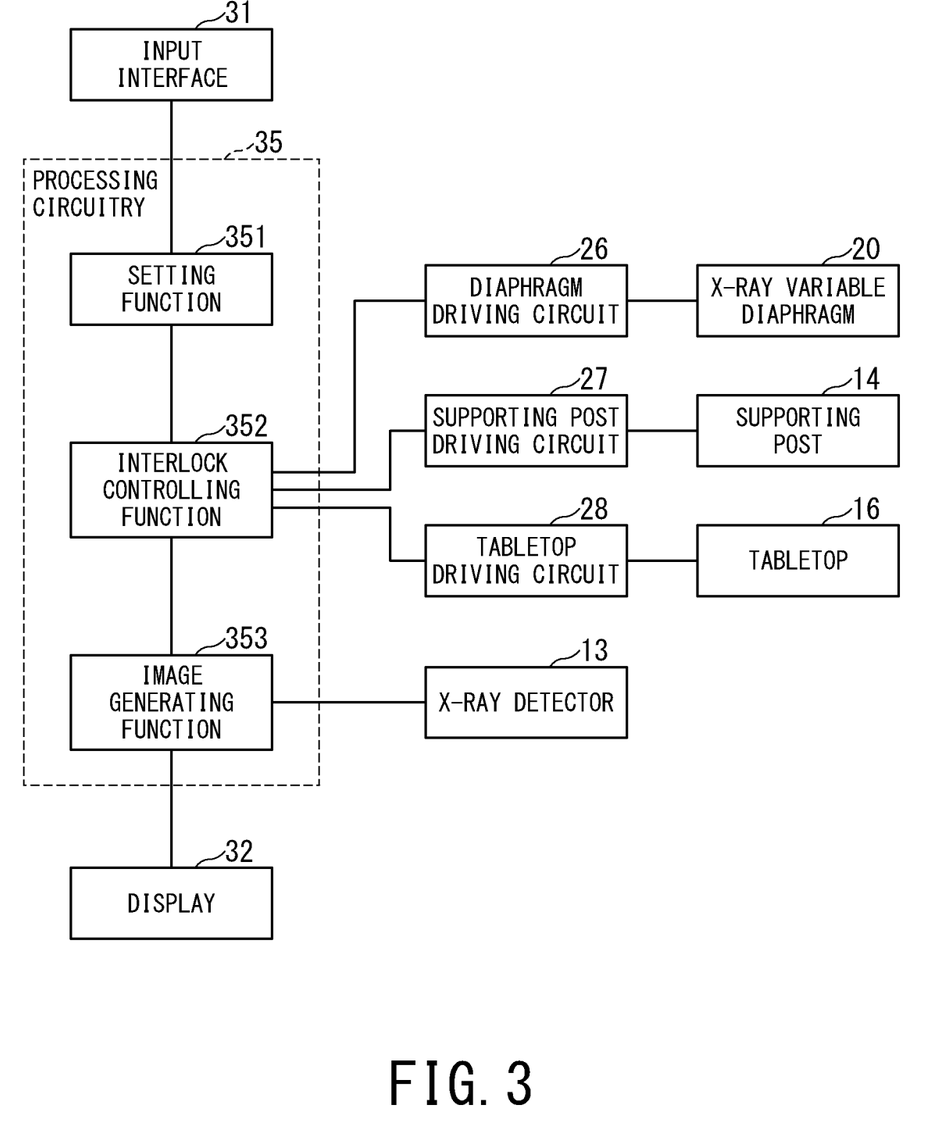
FIG. 3 is a schematic block diagram showing an example of functions realized by processing circuitry.

FIG. 3 is a schematic block diagram showing an example of functions realized by the processing circuitry 35. As shown in FIG. 3, the processor of the processing circuitry 35 realizes a setting function 351, an interlock controlling function 352, and an image generating function 353. Each of these functions is stored in the memory 33 in the form of a program.

The setting function 351, based on the user's instruction via the region movement instruction lever 312 of the input interface 31, sets the imaging range having a width larger than the width of the X-ray detector 13 in a predetermined direction parallel to the surface of the tabletop 16 (hereinafter referred to as the "set direction of movement"), the size of the irradiation region of X-rays, and the direction of movement of the irradiation region in the imaging range as the set direction of movement.

The interlock controlling function 352 enables the irradiation region to move at a constant velocity in the set direction of movement relative to the surface of the tabletop 16. For this purpose, the interlock controlling function 352 controls the diaphragm driving circuit 26 and the supporting post driving circuit 27 according to the positional relationship between the irradiation region and the X-ray detector 13. The diaphragm driving circuit 26 and the supporting post driving circuit 27 are controlled such that the movement of the aperture 25 of the X-ray variable diaphragm 20 in the set direction of movement made by the diaphragm driving circuit 26 and the movement of the supporting post 14 in the set direction of movement made by the supporting post driving circuit 27 of the supporting post driving mechanism 15 are linked (interlocked).

The diaphragm driving circuit 26 determines the size of the aperture 25 of the X-ray variable diaphragm 20 according to the size of the set irradiation region. Further, the diaphragm driving circuit 26 is controlled by the interlock controlling function 352 to move the position of the aperture 25 parallel to the surface of the tabletop 16 according to the set direction of movement.

Figure 4:
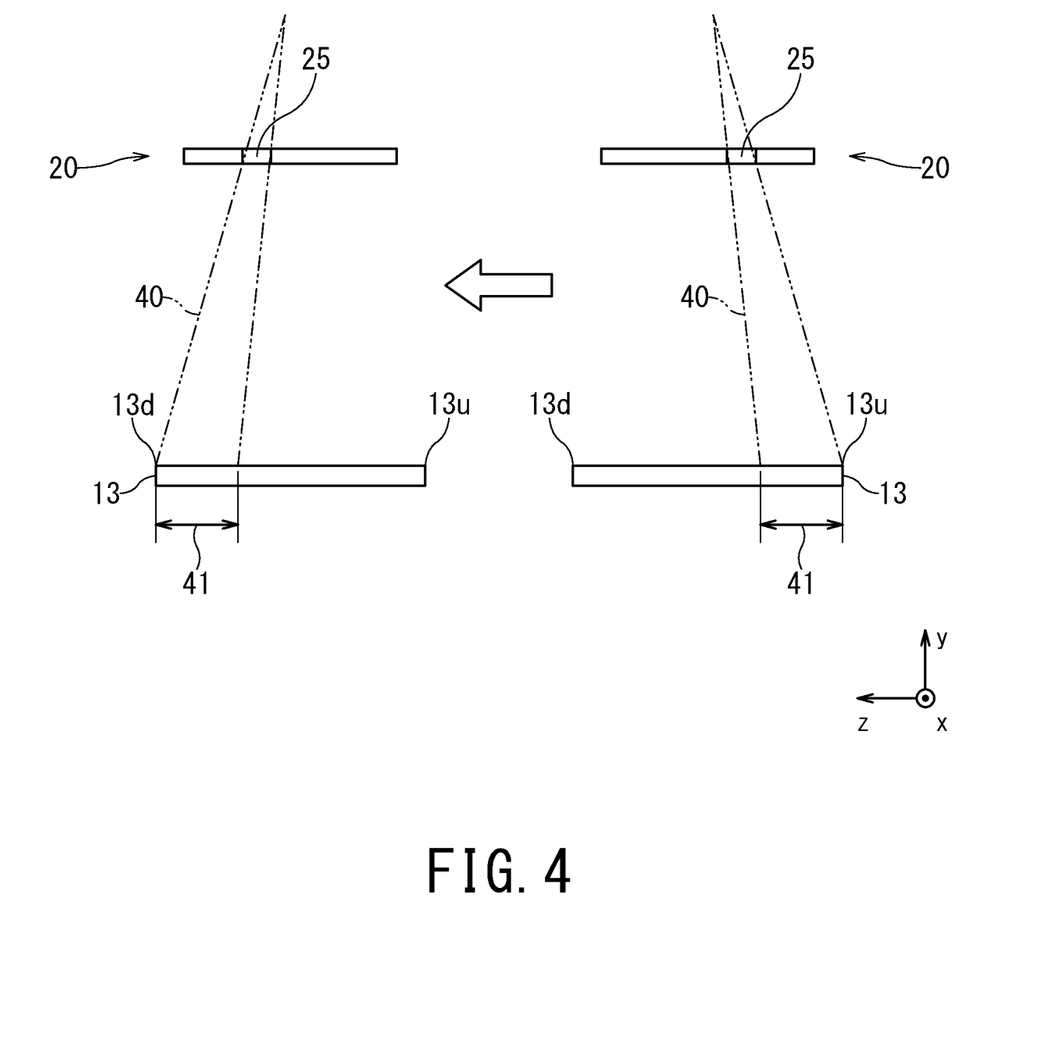
FIG. 4 is an explanatory diagram showing an example of a relationship between an aperture and an irradiation region.

FIG. 4 is an explanatory diagram showing an example of a relationship between the aperture 25 and the irradiation region 41. FIG. 4 shows an example where the set direction of movement is positive in the z direction.

By moving the aperture 25 in the set direction of movement, the X-ray flux 40 can be moved. Therefore, even if the X-ray source 11 and the X-ray detector 13 remain stationary, the irradiation region 41 on the X-ray detector 13 can be moved from the upstream end 13$u$ to the downstream end 13$d$ of the X-ray detector 13 in the set direction of movement by moving the aperture 25 in the set direction of movement (see FIG. 4).

Figure 5A:
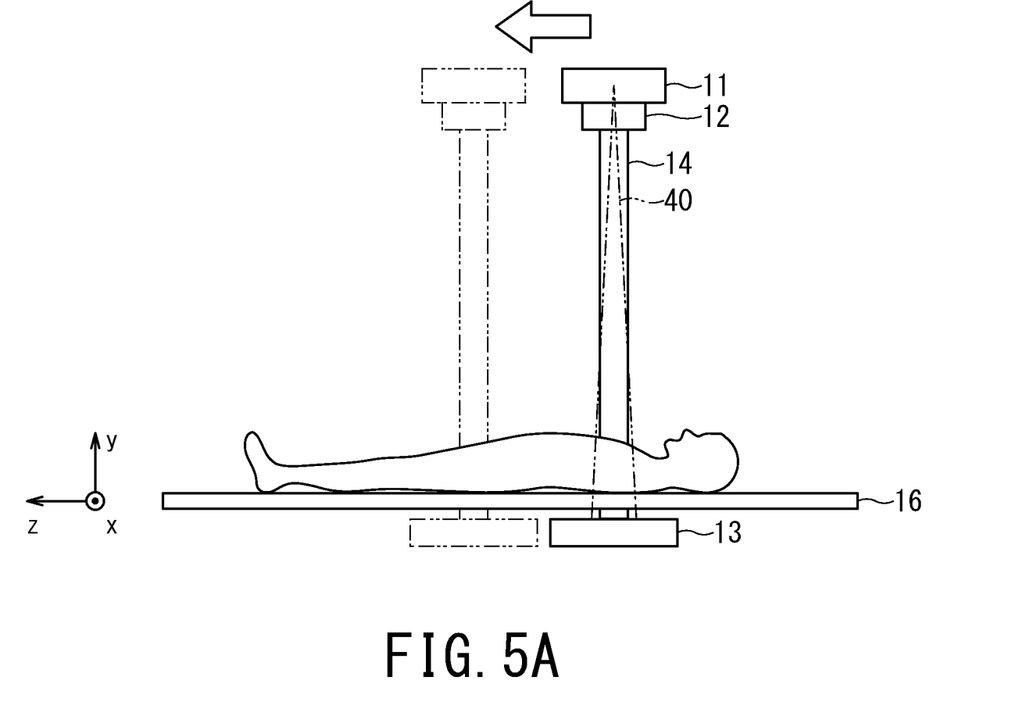
FIG. 5A is a side view for explaining an example of how a supporting post moves along a longitudinal direction of a tabletop.
Figure 5B:
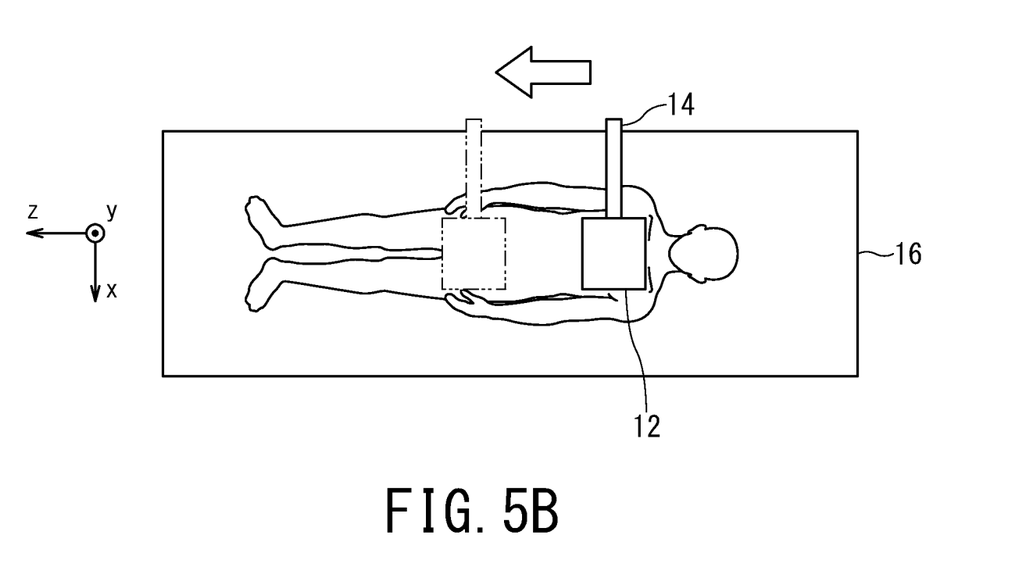
FIG. 5B is a top view for explaining an example of how a supporting post moves along a longitudinal direction of a tabletop.

FIG. 5A is a side view for explaining an example of how the supporting post 14 moves along the longitudinal direction of the tabletop 16, and FIG. 5B is a top view thereof.

The supporting post driving circuit 27 is controlled by the interlock controlling function 352 to move the supporting post 14 parallel to the surface of the tabletop 16 according to the set direction of movement, thereby moving the X-ray source 11, the housing 12, and the X-ray detector 13 as a single unit in the set direction of movement. As the X-ray source 11 moves, the X-ray flux 40 moves along the set direction of movement with respect to the surface of the tabletop 16.

Additionally, the interlock controlling function 352 may further interlock the movement of the tabletop 16 in the set direction of movement by the tabletop driving circuit 28 of the tabletop driving mechanism (not shown) with these movements.

The image generating function 353 generates an X-ray fluoroscopic image corresponding to the irradiation region 41 in real time and displays it on the display 32.

Figure 6A:
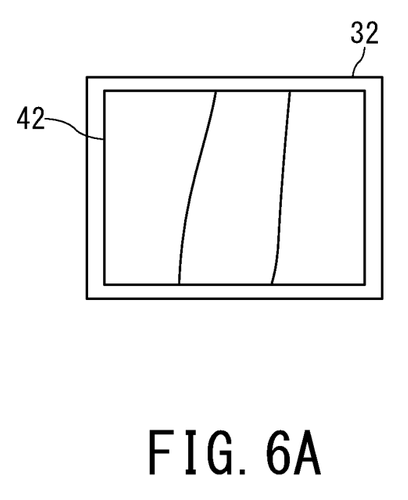
FIG. 6A is an explanatory diagram showing an example of a fluoroscopic image display area on a display.
Figure 6B:
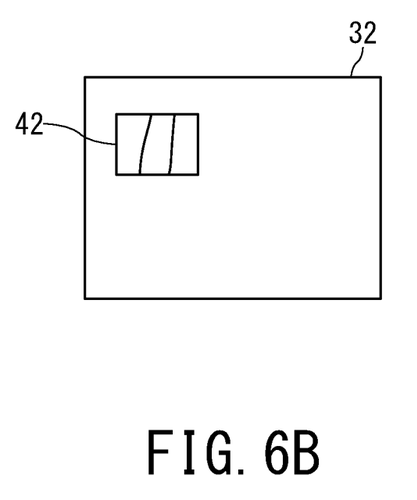
FIG. 6B is an explanatory diagram showing another example of a fluoroscopic image display area on a display.

FIG. 6A is an explanatory diagram showing an example of a fluoroscopic image display area 42 on the display 32, and FIG. 6B is another example thereof.

The image generating function 353 causes the fluoroscopic image corresponding to the irradiation region 41 to be displayed on the fluoroscopic image display area 42 on the display 32. The fluoroscopic image display area 42 may be set to occupy most of the display area on the display 32 (see FIG. 6A). In this case, since the fluoroscopic image corresponding to the irradiation region 41 can be enlarged, the user is able to observe the observation target in detail. The fluoroscopic image display area 42 may be a region corresponding to the position of the irradiation region 41 on the X-ray detector 13. In this case, the entire display area of the display 32 may be made to correspond to the entire detection surface of the X-ray detector 13 (see FIG. 6B). In this case, the user can easily and intuitively grasp the position of the current irradiation region 41 on the X-ray detector 13. These display methods can also be switched according to the user's instructions.

Next, an example of the operation of the X-ray diagnostic apparatus 10 of embodiments will be described.

Figure 7:
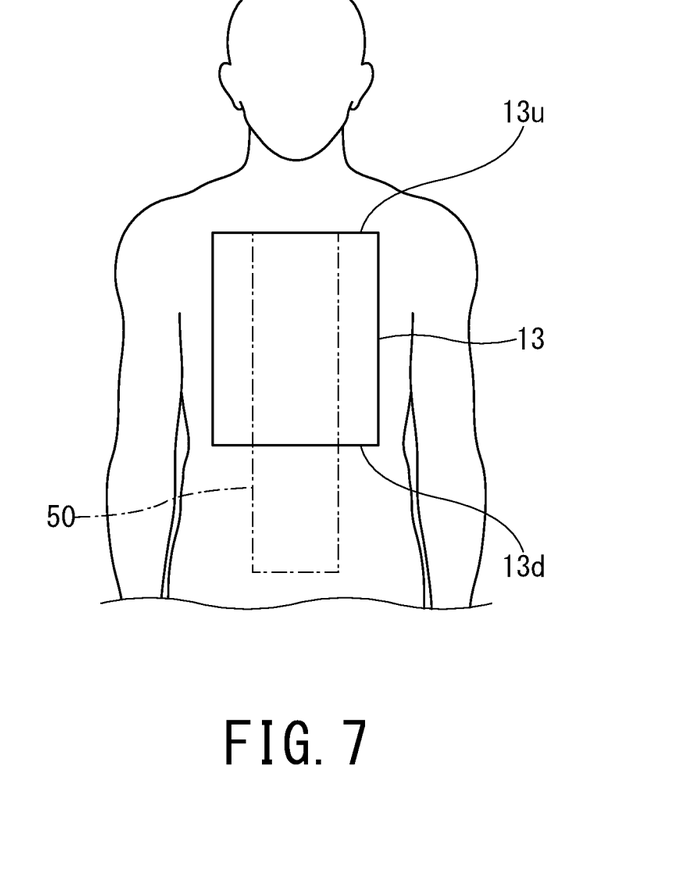
FIG. 7 is an explanatory diagram showing an example of a relationship between an X-ray detector and an imaging range.

FIG. 7 is an explanatory diagram showing an example of a relationship between the X-ray detector 13 and the imaging range 50.

As described above, the setting function 351 sets, based on instructions by the user through the input interface 31, the imaging range 50 having a width larger than the width of the X-ray detector 13 in the set direction of movement, the size of the X-ray irradiation region 41, and the direction of movement of the irradiation region 41 in the imaging range 50.

FIG. 7 shows an example where the set direction of movement is positive (from head to foot) in the z-axis direction (body axis direction). In the following, an example is shown where the width of the imaging range 50 is equal to the width of the irradiation region 41 in the direction orthogonal to the set direction of movement. In this case, the irradiation region 41 does not need to be moved in the direction orthogonal to the set direction of movement, and the entire range of the imaging range 50 can be fluoroscopically imaged by moving the irradiation region 41 in the set direction of movement. The upstream end 13$u$ and the downstream end 13$d$ of the X-ray detector 13 are defined by setting the set direction of movement.

Figure 8:
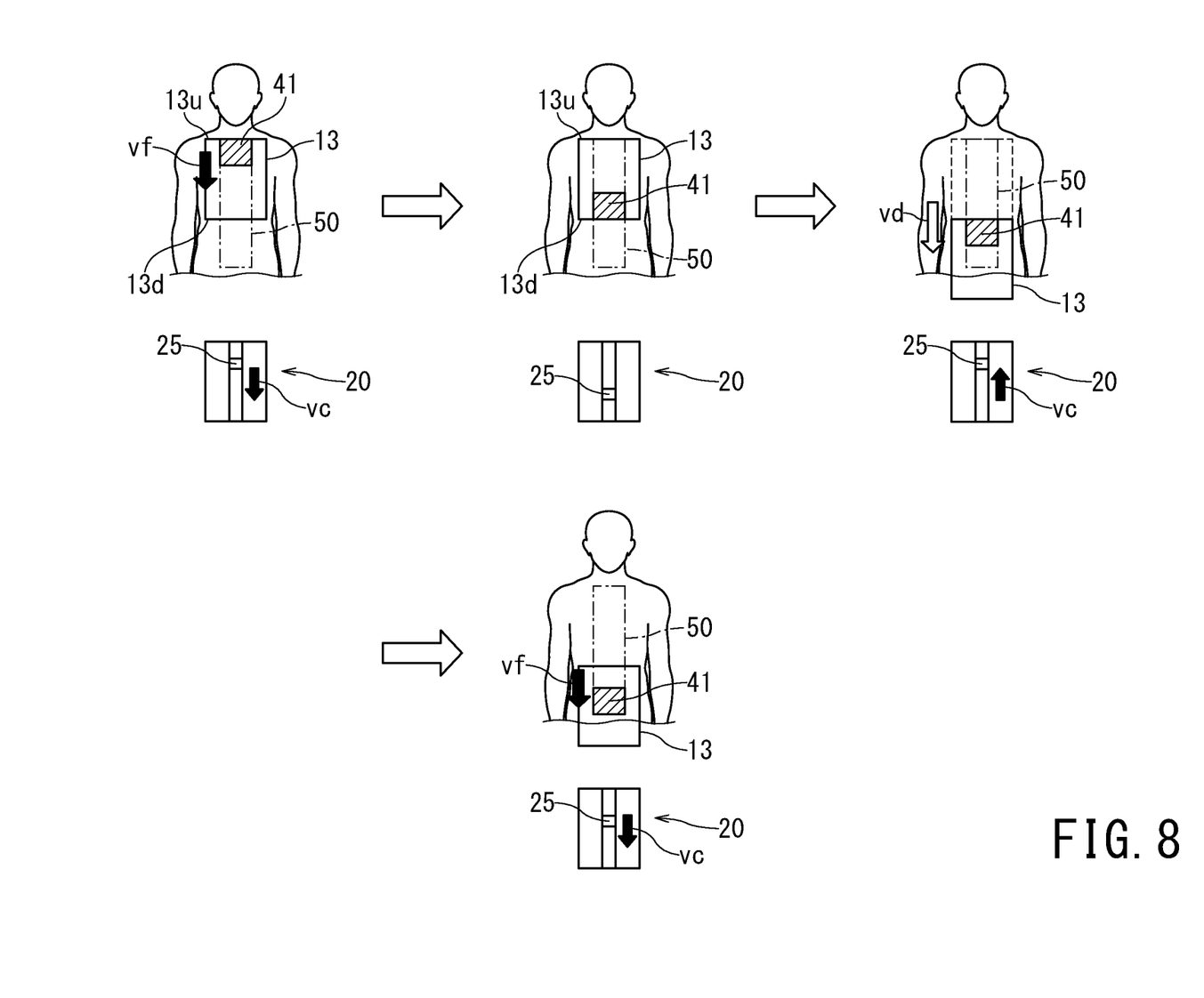
FIG. 8 is an explanatory diagram showing an example of how to move the irradiation region.

FIG. 8 is an explanatory diagram showing an example of how to move the irradiation region 41. Hereinafter, the method starting in a state where the upper end of the irradiation region 41 matches the upstream end 13$u$ of the X-ray detector 13 will be described.

First, the interlock controlling function 352 starts moving the aperture 25 of the X-ray variable diaphragm 20 at a constant velocity vc such that the supporting post 14 is not moved and the irradiation region 41 is moved at a constant velocity vf. The movement velocity vc of the aperture 25 is defined as the velocity of the aperture 25 relative to the housing 12, for example. The movement velocity vf of the irradiation region 41 may be defined as the velocity on the top surface of the tabletop 16, on the object, or on the X-ray detector 13.

Next, when the lower end of the irradiation region 41 reaches the downstream end 13$d$ of the X-ray detector 13 (see the upper center of FIG. 8), in order to move the X-ray detector 13 to the next region adjacent to the downstream side of the current region, the interlock controlling function 352 moves the X-ray detector 13 (i.e., supporting post 14) at a velocity vd by the width of the X-ray detector 13 in the set direction of movement, and also moves the aperture 25 at a velocity vc such that the upstream end 13$u$ of the moved X-ray detector 13 coincides with the upper edge of the irradiation region 41 (see the upper right of FIG. 8). At this time, the direction of the velocity vc (negative in the z-axis direction) is opposite to the set direction of movement, and it is preferable that the movement of the X-ray detector 13 and the movement of the aperture 25 are performed concurrently. The moving velocity vd of the X-ray detector 13 may be defined as the velocity of the X-ray detector 13 relative to the tabletop 16.

Next, the interlock controlling function 352 starts to move the aperture 25 of the X-ray variable diaphragm 20 at the constant velocity vc again such that the irradiation region 41 is moved at the constant velocity of while the supporting post 14 remains stationary (see the lower part of FIG. 8).

When the lower end of the irradiation region 41 reaches the downstream end 13d of the X-ray detector 13, and the user manually adjusts the position of the imaging system, the user has to constantly check on whether the current irradiation region 41 extends beyond the X-ray detector 13 or not. Also, the user further needs to suspend observation so as to adjust the position of the imaging system by operating the supporting post movement instruction lever 311 and the position of the irradiation region by operating the region movement instruction lever 312.

According to the method shown in FIG. 8, even when imaging range 50 is wider than the width of X-ray detector 13, the user only needs to indicate the direction of movement of the irradiation region 41 via the region movement instruction lever 312, without operating the supporting post movement instruction lever 311, and then the interlock controlling function 352 automatically moves the irradiation region 41 relative to the object, whereby the user can observe the fluoroscopic images through the entire imaging range 50 smoothly. Further, according to the method shown in FIG. 8, the user is not only free from the burden of manipulations, but also does not need to check on whether the current irradiation region 41 protrudes from the X-ray detector 13 or not. In addition, the imaging range 50 can be observed in a much shorter time compared with the case of manually adjusting the position of the imaging system, thus the exposure dose of the object can be reduced.

Figure 9:
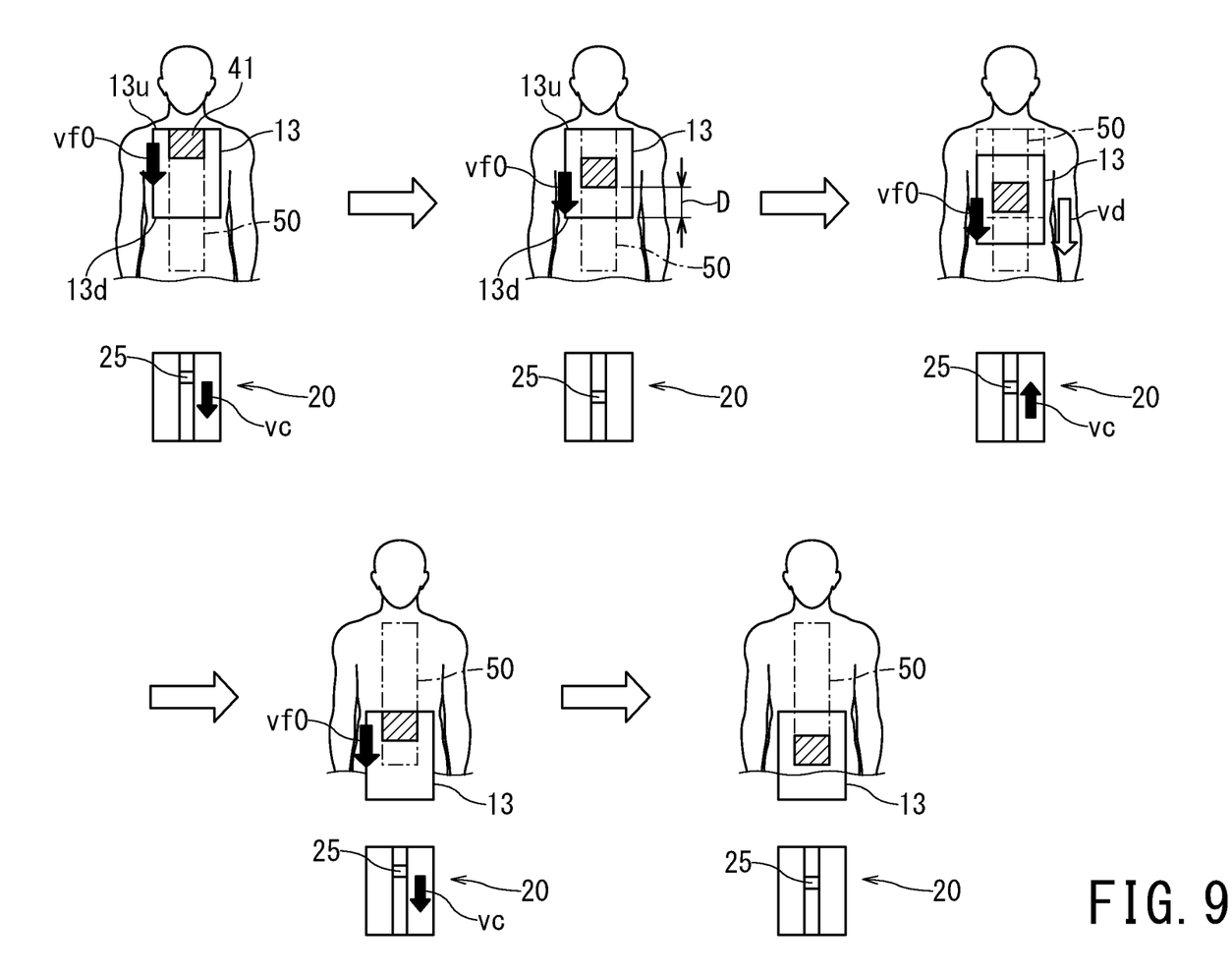
FIG. 9 is an explanatory diagram showing an example of how to move the irradiation region at a constant velocity.

FIG. 9 is an explanatory diagram showing an example of how to move the irradiation region 41 at a constant velocity vf0.

In the method shown in FIG. 9, the movement of the X-ray detector 13 is started before the lower end of the irradiation region 41 reaches the downstream end 13d of the X-ray detector 13, whereby the irradiation region 41 can move at the constant velocity vf0 in the entire imaging range 50.

Specifically, when the position of the lower end of the irradiation region 41 on the X-ray detector 13 is upstream from the downstream end 13d of the X-ray detector 13 more than the predetermined distance D, the interlock controlling function 352 does not move the supporting post 14, but moves the aperture 25 of the X-ray variable diaphragm 20 at the constant velocity vc such that the irradiation region 41 moves at the constant velocity vf0 (see upper left of FIG. 9).

The speed of the constant velocity vf0 of the irradiation region 41 may be set by the user or automatically set according to the size of the irradiation region 41.

When the position of the irradiation region 41 on the X-ray detector 13 is reached within the predetermined distance D from the downstream end 13d (see upper center of FIG. 9), the interlock controlling function 352 moves the aperture 25 at velocity vc and concurrently moves the X-ray detector 13 at velocity vd such that the velocity vf0 of the irradiation region 41 is maintained (see upper right of FIG. 9). More specifically, the interlock controlling function 352 controls the velocity vc of the aperture 25 and the velocity vd of the X-ray detector 13 in conjunction with each other, depending on their positions, such that the velocity vf0 of the irradiation region 41 is maintained.

At this time, the interlock controlling function 352 may also control the speed and orientation of the velocity vc of the aperture 25 as well as the speed and orientation of the velocity vd of the X-ray detector 13, such that the timing when the X-ray detector 13 completes the movement to the next region and the timing when the upper end of the irradiation region 41 matches the upstream end 13u of the X-ray detector 13 after moving to the next region are simultaneous (see lower left of FIG. 9). When the X-ray detector 13 finishes moving to the next region, the supporting post 14 is stopped and the aperture 25 is moved at the constant velocity vc such that the irradiation region 41 is moved at the constant velocity vf0 (see lower right of FIG. 9).

The method shown in FIG. 9 has the same effect as the method shown in FIG. 8. Further, the method shown in FIG. 9 allows fluoroscopic observation of the entire imaging range 50 to be performed while the moving velocity vf0 of the irradiation region 41 remains constant.

In addition, compared to the method shown in FIG. 8, the method shown in FIG. 9 does not require the time from when the lower end of the irradiation region 41 reaches the downstream end 13d of the X-ray detector 13 until the fluoroscopy of the next region is resumed. Therefore, the method shown in FIG. 9 can further shorten the inspection time than the method shown in FIG. 8, and can significantly reduce the exposure dose of the object.

The method shown in FIG. 9 can start the movement of the X-ray detector 13 before the lower end of the irradiation region 41 reaches the downstream end 13d of the X-ray detector 13 and control the movement of the X-ray detector 13 in conjunction with the movement of the aperture 25, and thus, the velocity of the irradiation region 41 can be easily maintained at the constant velocity vf0 even during the acceleration period immediately after the X-ray detector 13 starts to move.

Figure 10:
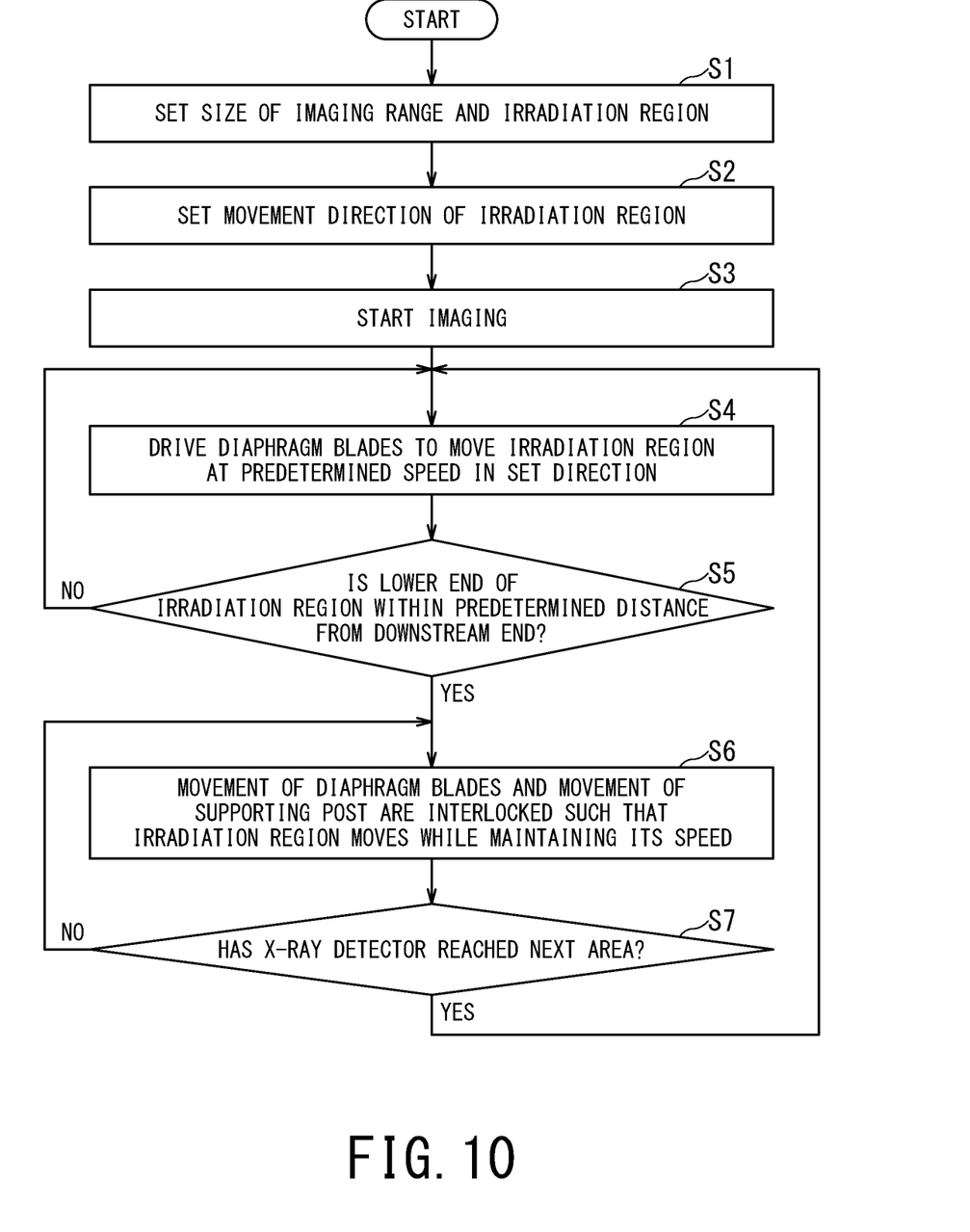
FIG. 10 is a flowchart showing an example of a procedure of a process for performing automatic fluoroscopy of the imaging range wider than the width of the X-ray detector while moving the X-ray irradiation region at a constant velocity relative to the object by the processor of the processing circuitry.

FIG. 10 is a flowchart showing an example of a procedure of a process for performing automatic fluoroscopy of the imaging range 50 wider than the width of the X-ray detector 13 while moving the X-ray irradiation region 41 at the constant velocity vf0 relative to the object by the processor of the processing circuitry 35. In FIG. 10, reference numerals with numbers attached to S indicates each step of the flowchart. The procedure shown in FIG. 10 corresponds to the method shown in FIG. 9.

First, in step S1, the setting function 351 sets the size of the imaging range 50 and irradiation region 41 based on the instructions given by the user through the input interface 31.

Next, in step S2, the setting function 351 sets the direction of movement of the irradiation region 41 in the imaging range 50 based on the instructions given by the user via the region movement instruction lever 312 of the input interface 31.

When the fluoroscopy of the imaging range 50 is started (step S3), in step S4, the interlock controlling function 352 moves the aperture 25 of the X-ray variable diaphragm 20 at the constant velocity vc such that the irradiation region 41 moves at the constant velocity vf0 (see upper left of FIG. 9).

Next, in step S5, the interlock controlling function 352 determines whether the position on the X-ray detector 13 of the lower end of the irradiation region 41 is within the predetermined distance D from the downstream end 13d of the X-ray detector 13.

When the lower end of the irradiation region 41 on the X-ray detector 13 is more upstream than the predetermined distance D from the downstream end 13d of the X-ray detector 13, the procedure returns to step S4.

Meanwhile, when the lower end of the irradiation region 41 on the X-ray detector 13 is within the predetermined distance D from the downstream end 13d of the X-ray detector 13, in step S6, the interlock controlling function 352 interlocks the movement of the aperture 25 and the movement of the X-ray detector 13 such that the irradiation region 41 moves maintaining the constant velocity vf0 (see upper right of FIG. 9).

Until the X-ray detector 13 reaches the next area adjacent to the downstream side (NO in step S7), the process in step S6 is repeated. When the X-ray detector 13 reaches the next area adjacent to the downstream side (YES in step S7), the procedure returns to step S4. When the lower end of the irradiation region 41 reaches the lower end of the imaging range 50, the procedures come to an end.

In the above manner, by the method shown in FIG. 9 is executed, an automatic fluoroscopy of the imaging range 50, which is wider than the width of the X-ray detector 13, can be performed while moving the X-ray irradiation region 41 at the constant velocity vf0 relative to the object. Therefore, the user can observe the fluoroscopic images of the imaging range 50 smoothly at the constant velocity from the beginning to the end.

Figure 11:
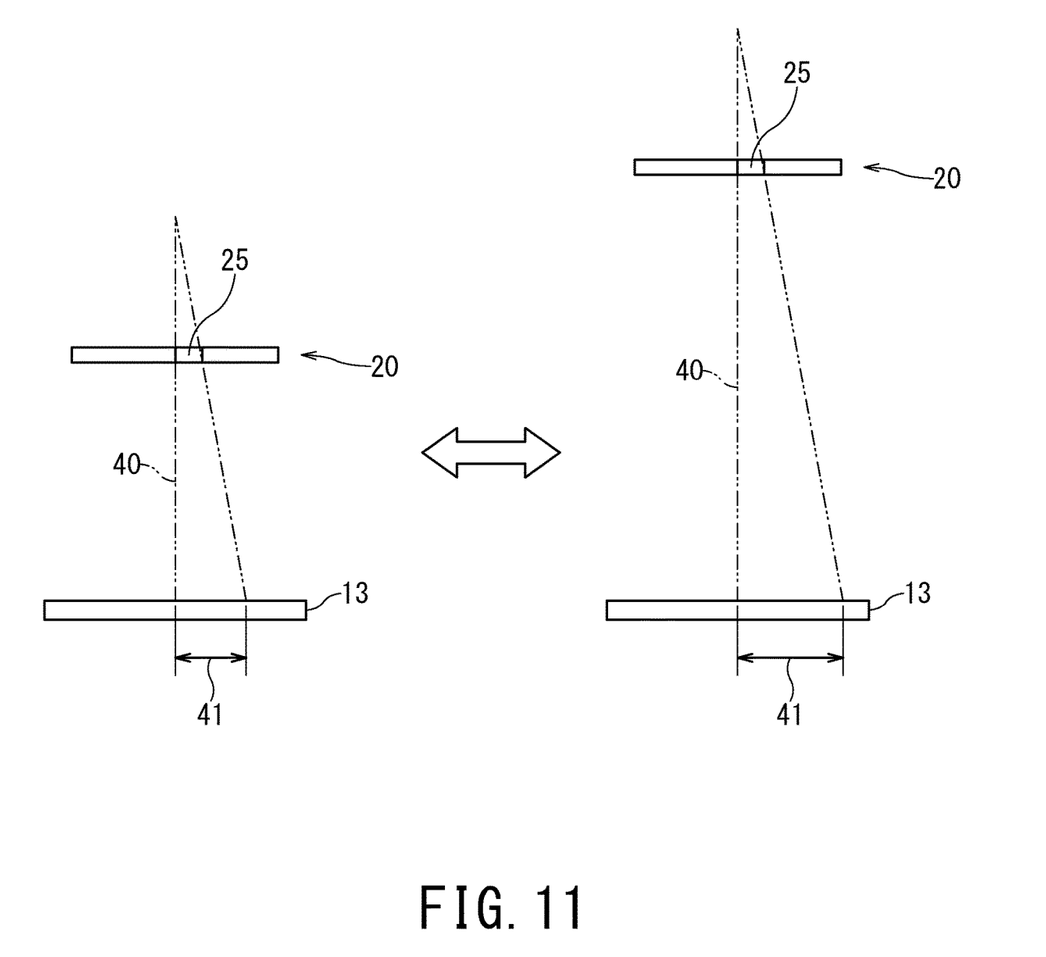
FIG. 11 is a diagram for explaining an example of a case where the size of the irradiation region changes.

FIG. 11 is a diagram for explaining an example of a case where the size of the irradiation region 41 changes.

The size of the irradiation region 41 is uniquely determined by the size of the aperture 25 and the source-to-image distance (SID). Therefore, when the size of the aperture 25 is the same, the irradiation region 41 becomes larger as the Source to image Distance (SID) becomes longer, as shown in FIG. 11. Also, when the movement velocity vc of the aperture 25 is constant, the movement velocity of the irradiation region 41 becomes faster as the SID becomes longer. Therefore, when the SID is changed during fluoroscopy of imaging range 50, the moving velocity of irradiation region 41 will change, and the user may have difficulty observing the observation target.

Therefore, the interlock controlling function 352 is preferably designed to move the irradiation region 41 at the constant velocity vf0 even when the size of the irradiation region 41 is changed during fluoroscopy of the imaging range 50. It is recommended to control the movement velocity vc of the aperture 25 and the movement velocity vd of the X-ray detector 13 according to the size of the irradiation region 41 such that the irradiation region 41 moves at the constant velocity vf0 even when the size of the irradiation region 41 is changed during fluoroscopy of the imaging range 50.

When the enlarged display method shown in FIG. 6A is adopted, the smaller the irradiation region 41 is, the finer the observation image becomes. However, when the irradiation region 41 is small, it is easy to lose sight of the observation target if the velocity of the irradiation region 41 is fast. Meanwhile, when the irradiation region 41 is large, it is difficult to find the observation target if the movement velocity of the irradiation region 41 is slow, which makes operation difficult. Therefore, the interlock controlling function 352 is preferably designed such that the smaller the irradiation region 41 set by the setting function 351 is, the slower the constant velocity vf0 of irradiation region 41 becomes.

According to at least one of the above-described embodiments, the imaging range wider than the width of the X-ray detector can be automatically fluoroscoped while moving the X-ray irradiation region at a constant velocity relative to the object.

The processing circuitry in the above-described embodiments is an example of the processing circuitry described in the claims. In addition, the term "processor" used in the explanation in the above-described embodiments, for instance, refers to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing the corresponding program. When a plurality of processors is provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
   an X-ray tube irradiating X-rays;
   an X-ray variable diaphragm limiting an irradiation region of the X-rays;
   an X-ray detector detecting the X-rays that have passed through an object; and
   processing circuitry configured to control a movement of the X-ray tube, the X-ray detector, and an aperture of the X-ray variable diaphragm such that, when the irradiation region on the X-ray detector moves within an imaging range, a movement velocity of the irradiation region relative to the imaging range is maintained constant,
   wherein:
   the processing circuitry is further configured,
      when a position of a lower end of the irradiation region on the X-ray detector is upstream from a downstream end of the X-ray detector more than a predetermined distance, to move the aperture of the X-ray variable diaphragm and not move the X-ray tube and the X-ray detector such that the movement velocity of the irradiation region is maintained constant; and
      when the position of the lower end of the irradiation region on the X-ray detector is reached within the predetermined distance from the downstream end, to control the movement of the aperture and the movement of the X-ray tube and the X-ray detector in conjunction with each other such that the movement velocity of the irradiation region is maintained constant.

2. The X-ray diagnostic apparatus according to claim 1, wherein, when a size of the irradiation region is changed during imaging of the imaging range, the processing circuitry controls the movement of the X-ray tube, the X-ray detector, and the aperture of the X-ray variable diaphragm such that the movement velocity of the irradiation region relative to the imaging range is maintained constant before and after the size of the irradiation region changes.

3. The X-ray diagnostic apparatus according to claim 1, wherein the processing circuitry controls the movement of the X-ray tube, X-ray detector, and X-ray variable diaphragm apertures such that the smaller the set irradiating region, the slower the moving velocity of the irradiating region relative to the imaging range that is controlled to be maintained constant.

4. The X-ray diagnostic apparatus according to claim 1, wherein the processing circuitry generates an X-ray fluoroscopic image corresponding to the irradiated region in real time and displays it on a display.

5. The X-ray diagnostic apparatus according to claim 1 further comprising:
a support member that supports the X-ray tube, the X-ray variable diaphragm, and the X-ray detector detecting the X-rays that have passed through the object placed on a tabletop such that the X-ray tube and the X-ray variable diaphragm face the X-ray detector across the tabletop;
a diaphragm driving circuit that determines a size of the aperture of the X-ray variable diaphragm according to a size of the irradiation region set by the processing circuitry and moves a position of the aperture parallel to a surface of the tabletop according to a direction of the movement that is parallel to the surface of the tabletop and is set by the processing circuitry; and
a support member driving circuit that moves the support member parallel to the surface of the tabletop according to the direction of the movement set by the processing circuitry,
wherein
the processing circuitry sets the imaging range having a width larger than a width of the X-ray detector in the direction of the movement, the size of the irradiation region, and the direction of the movement of the irradiation region on the imaging range, and
the processing circuitry controls the support member driving circuit and the diaphragm driving circuit according to the positional relationship between the irradiation region and the X-ray detector such that the irradiation region moves at the constant velocity relative to the imaging range, wherein the support member driving circuit and the diaphragm driving circuit are controlled such that a movement of the aperture of the X-ray variable diaphragm in the direction made by the diaphragm driving circuit interlocks with a movement of the support member in the direction made by the support member driving circuit.

6. The X-ray diagnostic apparatus according to claim 5, wherein
when a position of the irradiation region on the X-ray detector is more than a predetermined distance upstream from a downstream end of the X-ray detector in the direction of the movement, the processing circuitry moves the position of the irradiation region on the X-ray detector in the direction by moving the position of the aperture without moving the support member such that the irradiation region moves at the constant velocity relative to the surface of the tabletop, and
when the position of the irradiation region on the X-ray detector reaches within the predetermined distance from the downstream end, the processing circuitry interlocks the movement of the aperture in the direction with the movement of the support member in the direction such that the irradiation region maintains the constant velocity of movement relative to the surface of the tabletop.

7. The X-ray diagnostic apparatus according to claim 5 further comprising a tabletop driving circuit that moves the tabletop parallel to its surface according to the direction of the movement set by the processing circuitry,
wherein the processing circuitry controls the tabletop driving circuit, the diaphragm driving circuit, and the support member driving circuit according to the positional relationship between the irradiation region and the X-ray detector such that the irradiation region moves at the constant velocity relative to the surface of the tabletop.

8. A control method of an X-ray diagnostic apparatus that includes an X-ray tube irradiating X-rays, an X-ray variable diaphragm limiting an irradiation region of the X-rays, and an X-ray detector detecting the X-rays that have passed through an object, the method comprising:
setting a movement velocity of the irradiation region relative to an imaging range; and
controlling a movement of the X-ray tube, the X-ray detector, and an aperture of the X-ray variable diaphragm such that, when the irradiation region on the X-ray detector moves within the imaging range, the set movement velocity of the irradiation region relative to the imaging range is maintained constant, including
when a position of a lower end of the irradiation region on the X-ray detector is upstream from a downstream end of the X-ray detector more than a predetermined distance, moving the aperture of the X-ray variable diaphragm and not moving the X-ray tube and the X-ray detector such that the movement velocity of the irradiation region is maintained constant; and
when the position of the lower end of the irradiation region on the X-ray detector is reached within the predetermined distance from the downstream end, controlling the movement of the aperture and the movement of the X-ray tube and the X-ray detector in conjunction with each other such that the movement velocity of the irradiation region is maintained constant.

9. An X-ray diagnostic apparatus comprising:
an X-ray tube irradiating X-rays;
an X-ray variable diaphragm limiting an irradiation region of the X-rays;
an X-ray detector detecting the X-rays that have passed through an object; and
processing circuitry configured to control a movement of the X-ray tube, the X-ray detector, and an aperture of the X-ray variable diaphragm such that, when the irradiation region on the X-ray detector moves within an imaging range, a movement velocity of the irradiation region relative to the imaging range is maintained constant, the processing circuitry controlling the movement of the X-ray tube, X-ray detector, and X-ray variable diaphragm apertures such that the smaller the set irradiating region, the slower the moving velocity of the irradiating region relative to the imaging range that is controlled to be maintained constant.

* * * * *